United States Patent [19]
Koch

[11] 3,941,780
[45] Mar. 2, 1976

[54] COUMARIN COMPOUNDS

[75] Inventor: Werner Koch, Oberwil, Switzerland

[73] Assignee: Sandoz Ltd., (Sandoz AG), Basel, Switzerland

[22] Filed: Aug. 27, 1973

[21] Appl. No.: 391,568

[30] Foreign Application Priority Data
Aug. 29, 1972  Switzerland............... 12721/72

[52] U.S. Cl................. 260/243 D; 260/37 N
[51] Int. Cl.²................. C07D 285/24
[58] Field of Search................. 260/243 D

[56] References Cited
UNITED STATES PATENTS
3,311,620  3/1967  Bell et al............... 260/243 D
3,461,122  8/1969  Wei et al............... 260/243 D FOREIGN PATENTS OR APPLICATIONS
1,802,863  7/1970  Germany
465,551  1/1969  Switzerland

*Primary Examiner*—Paul M. Coughlan, Jr.
*Attorney, Agent, or Firm*—Gerald D. Sharkin; Richard E. Vila; Joseph J. Borovian

[57] ABSTRACT

The invention relates to compounds of formula I,

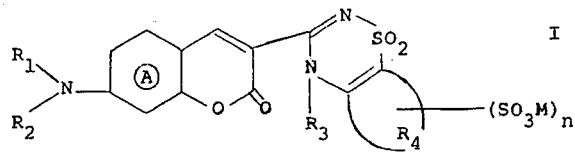

in which either, each of $R_1$ and $R_2$, which may be the same or different, signifies a hydrogen atom or an unsubstituted or substituted ($C_{1-7}$) alkyl or ($C_{2-7}$) alkenyl radical, with the proviso that that when one of $R_1$ and $R_2$ signifies a hydrogen atom, the other has a significance other than hydrogen, or $R_1$ and $R_2$, together with the nitrogen atom to which they are attached, from a five or six-membered substituted or unsubstituted heterocyclic ring system, $R_3$ signifies a hydrogen atom or an unsubsstituted ($C_{1-7}$) alkyl radical, $R_4$ signifies the atoms necessary to complete an aromatic carbocyclic or heterocyclic ring system, which ring system in addition to bearing up to two sulphonic groups is further unsubstituted or further substituted, M is hydrogen or alkali metal, n is 1 or 2, and the ring A is further unsubstituted or further substituted, which compounds are useful as water-soluble fluorescent dyes.

19 Claims, No Drawings

COUMARIN COMPOUNDS

The invention relates to water soluble fluorescent coumarin dyes.

The present invention provides compounds of formula I,

I in which either, each of $R_1$ and $R_2$, which may be the same or different, signifies a hydrogen atom or an unsubstituted or substituted alkyl or alkenyl radical, which alkyl radical contains 1 to 7 carbon atoms, and which alkenyl radical contains 2 to 7 carbon atoms, with the proviso that when one of $R_1$ and $R_2$ signifies a hydrogen atom, the other has a significance other than hydrogen, or $R_1$ and $R_2$, together with the nitrogen atom to which they are attached, from a five or six-membered substituted or unsubstituted heterocyclic ring system, $R_3$ signifies a hydrogen atom or an unsubstituted alkyl radical, which alkyl radical contains 1 to 7 carbon atoms, $R_4$ signifies the atoms necessary to complete an aromatic carbocyclic or heterocyclic ring system, which ring system in addition to bearing up to two sulphonic groups is further unsubstituted or further substituted, M is hydrogen or alkali metal, $n$ is 1 or 2, and the ring A is further unsubstituted or further substituted.

The invention also provides a process for the production of compounds of formula I, stated above, characterized by a. sulphonating a compound of formula VI or VII,

VI

VII in which $R_1$, $R_2$, $R_3$, $R_4$, $n$ and the Ring A are as defined above, b. reacting a compound of formula IV,

IV in which $R_3$, $R_4$ and $n$ are as defined above, with a compound of formula III.

III in which $R_1$, $R_2$ and the Ring A are as defined above, and hydrolyzing the resulting product.

Sulphonation may be carried out employing methods known per se, e.g. using oleum, which is preferably present in excess. Preferably, 20 to 30% oleum is employed. The sulphonation reaction may be started at 0°, but is is preferably carried out between 20° and 70°C and most advantageously, between 40° and 50°C. The indicated temperature range may be varied, however, corresponding to the sensitivity of the substituents present in the molecule to oleum.

The compounds of formula IV may be produced by sulphonating a compound of formula II,

II in which $R_3$ and $R_4$ are as defined above, in a manner analogous to known methods, for example as described above. Alternatively, a compound of formula V,

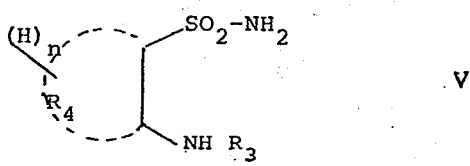

in which $R_3$, $R_4$ and $n$ are as defined above, may be sulphonated, and the resulting product treated with cyanoacetic acid or a functional derivative thereof to yield the compound of formula IV.

The compounds of formula VI may be obtained by reacting a compound of formula II with a compound of formula III, as defined above.

The reaction of the compounds of formulae II and III, or of the compounds of formula IV and formula III, may be effected in an inert, preferably anhydrous solvent, such as ethanol, methanol, dimethylformamide, dimethylsulphoxide or dioxane at temperatures from 30° to 180°, preferably at the boiling point of the solvent in question, under reflux, optionally in the presence of a basic catalyst, such as piperidine, pyrrolidine or pyridine.

The compounds of formula VI may be hydrolized in acid medium to produce the compounds of formula VII.

For the production of the compounds of formula I a compound of formula VI or of formula VII, may be employed since, during the course of sulphonation the =NH group in formula VI is hydrolized into =O.

Representative compounds of formula I include the compounds of formula I',

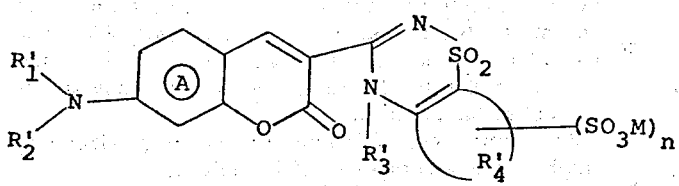

in which either, each of $R_1'$ and $R_2'$, which may be the same or different, signifies a hydrogen atom, an unsubstituted alkyl or alkenyl radical, or an alkyl radical substituted by a halogen atom or a cyano or alkoxy group; or an alkenyl radical substituted by a halogen atom or an alkoxy, haloalkoxy or alkoxyalkoxy group, which alkyl radicals and alkoxy moieties in such radicals contain 1 to 7 carbon atoms, which alkenyl radicals containg 2 to 7 carbon atoms, with the proviso that when one of $R_1'$ and $R_2'$ signifies a hydrogen atom the other has a significance other than hydrogen, or $R_1'$ and $R_2'$, together with the nitrogen atom to which they are attached, form a five or six-membered unsubstituted or alkyl substituted saturated heterocyclic ring, which ring contains no further hetero atom or one selected from oxygen, sulphur or nitrogen, $R_3'$ signifies a hydrogen atom or an unsubstituted alkyl radical of 1 to 4 carbon atoms $R_4'$ signifies the atoms necessary to complete a benzene, pyridine, pyrimidine, pyrryl, pyrazolyl, imidazolyl, naphthalene, quinoline or indole ring system, which rings, in addition to bearing up to two sulpho groups, are further unsubstituted or are further substituted by up to two substituents selected from halogen, alkyl, alkoxy, cyano, thiocyano, mono- and dialkylamino, phenylamino, N-phenyl-N-alkyl-amino, phenyl, halophenyl, cyanophenyl, alkyl-phenyl, alkoxyphenyl, sulpho-phenyl, phenoxy, vinyl, trifluoromethyl, $R''-Y-$, $R''-Y-O-$, $R''-Y-NH-$, $R'''-Z$, $R'''-Z-O$ and $R'''-Z-NH-$ in which $R''$ signifies an unsubstituted alkyl radical or an alkyl radical substituted by up to two substituents selected from halogen, alkoxy, cyano, alkylamino, phenyl and phenoxy groups, $R'''$ signifies a hydrogen atom or has the same significance as $R''$, Y signifies $-O-CO-$, $-SO_2-$ or $-O-SO_2-$ and Z signifies $-CO-$, $-NR'''CO-$ or $-NR'''SO_2-$ in which $R'''$ is as defined above, any alkyl radicals and alkyl and alkoxy moieties in such radicals contain 1 to 7 carbon atoms, ring A is further unsubstituted or substituted by up to two substituents selected from halogen atoms, alkyl, alkoxy or cyano groups, which alkyl and alkoxy groups contain 1 to 7 carbon atoms, and M and $n$ are as defined above.

Preferably, all alkyl and alkoxy groups and moieties in the compounds of formula I' contain 1 to 4 carbon atoms and all alkenyl groups contain 2 to 4 carbon atoms.

In the compounds of formula I' where $R_1'$ and $R_2'$ together with the nitrogen atom form a heterocyclic ring, suitable heterocyclic rings include pyrrolidine, piperidine, morpholine, thiomorpholine, piperazine and N-alkyl piperazine rings.

Preferred compounds of formula I include those of formula Ia,

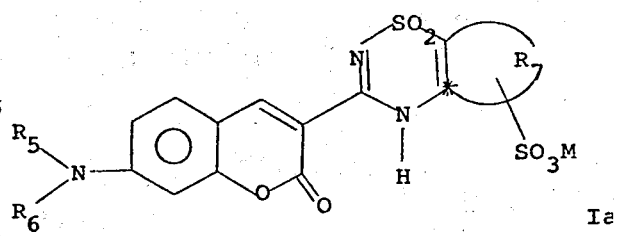

in which each of $R_5$ and $R_6$, which may be the same or different, signifies a hydrogen atom, an alkyl or allyl, radical or an alkyl radical substituted by a halogen atom, an alkoxy or cyano group, which alkyl radicals and alkoxy moieties in such radicals contain 1 to 4 carbon atoms with the proviso that when one of $R_5$ and $R_6$ signifies a hydrogen atom the other has a significance other than hydrogen, $R_7$ signifies a radical of formula (a), (b), (c), (d) or (e)

$$\left[ \begin{array}{cc} R_{21} & R_{20} \\ -C=N & -C=N^* \end{array} \right] \quad (a)$$

$$\left[ \begin{array}{ccc} R_{21} & R_{22} & R_{23} \\ -C=N & -C=C^* \end{array} \right] \quad (b)$$

$$\left[ \begin{array}{ccc} R_{21} & R_{22} & R_{23} \\ -C=C & -C=N^* \end{array} \right] \quad (c)$$

$$\left[ \begin{array}{cccc} R_{21} & R_{22} & R_{23} & R_{24} \\ -C=C & -C=C^* \end{array} \right] \quad (d)$$

or (e) [structure with $R_{11}$, $R_{10}$, H, and aromatic ring]

in which
$R_{20}$ signifies $SO_3M$,
$R_{21}$ signifies a hydrogen chlorine or bromine atom, a alkyl, alkoxy, cyano, thiocyano, trifluoromethyl, alkoxycarbonyl, benzyloxy-carbonyl, alkylcarbonyloxy, alkylcarbonylamino, amino-sulphonyl, alkylamino-sulphonyl or dialkylamino-sulphonyl radical, which alkyl and alkoxy radicals or moieties in such radicals contain 1 to 4 carbon atoms, each of
$R_{22}$, $R_{23}$ and $R_{24}$, which may be the same or different, signifies a hydrogen, chlorine or bromine atom, a $SO_3M$, methyl, alkoxy, cyano, thiocyano, trifluoromethyl, alkoxycarbonyl, benzyloxycarbonyl, alkyl-carbonyloxy, alkylcarbonyl-amino, aminosulphonyl or alkylaminosulphonyl radical, which alkyl and alkoxy radicals or moieties in such radicals contain 1 to 4 carbon atoms, with the proviso that each of radicals of formula (a) (b) (c) and (d) bear only one —$SO_3M$ group and the radical of formula (d) bears not more than two substituents in addition to the —$SO_3M$ group,
$R_{10}$ signifies hydrogen, amino sulphonyl or —$SO_3M$,
$R_{11}$ signifies a hydrogen atom or —$SO_3M$ with the proviso that the radical of formula (e) contains only one —$SO_3M$ group, the atom of radical (a) to (e) marked *, being, in each case, bound to the carbon atom designated by the same mark in formula I$a$ and
M is as defined above.

More preferred compounds of formula I include those of formula I$b$,

[Structure Ib]

in which each of
$R_{11}$ and $R_{12}$, which may be the same or different, signifies a methyl or ethyl or allyl radical, or a methyl or ethyl radical substituted by a cyano or alkoxy group of 1 to 4 carbon atoms,
$R_{13}$ signifies a radical of formula (b'), or (d'), $$\left[ \begin{array}{ccc} R_{21}' & R_{22}' & R_{23}' \\ -C=N & -C=C^* \end{array} \right] \quad (b')$$

$$\left[ \begin{array}{cccc} R_{21}' & R_{22}' & R_{23}' & R_{24}' \\ -C=C & -C=C^* \end{array} \right] \quad (d')$$

in which
$R_{21}'$ signifies a hydrogen, chlorine or bromine atom, a methyl, methoxy, ethoxy, cyano, trifluoromethyl, alkoxycarbonyl, alkyl-carbonyloxy, alkylcarbonyl amino or aminosulphonyl radical which alkyl and alkoxy moieties contain 1 to 4 carbon atoms, each of
$R_{22}'$, $R_{23}'$ and $R_{24}'$, which may be the same or different, signifies a hydrogen, chlorine or bromine atom, a $SO_3M$, methyl, methoxy, ethoxy, cyano, trifluoromethyl alkoxycarbonyl, alkylcarbonyloxy, alkyl-carbonylamino or amino-sulphonyl radical, which alkyl and alkoxy moieties containg 1 to 4 carbon atoms, with the proviso that the radicals (b') and (d') bear only one —$SO_3M$ group and the radical (d') bears not more than two substituents in addition to the —$SO_3M$ group,
the mark * has the same significance as defined above, and
M is as defined above.

Even more preferred compounds include those of formula I$c$,

[Structure Ic]

in which

R₁₁ and R₁₂ are as defined in Claim 5, each of

R₁₄ signifies a hydrogen, chlorine or bromine atom, a methyl, methoxy, ethoxy or trifluoromethyl radical, each of R₁₅, R₁₆ and R₁₇ signifies —SO₃M or a hydrogen, chlorine or bromine atom, a methyl, methoxy, ethoxy or trifluoro-methyl radical, with the proviso that one of R₁₅, R₁₆ and R₁₇ signifies SO₃M and at least one of R₁₄, R₁₅, R₁₆ and R₁₇ signifies a hydrogen atom.

In the compounds of formulae Ia and Ib where R₇ and R₁₃ form, respectively, a six-membered ring system, and in the compound of formula Ic, the —SO₃M group is preferably para to the amino group, or when the para position is already substituted or when it signifies =N— the —SO₃M group is meta to the amino group.

As examples of alkyl and alkoxy radicals or moieties of 1 to 4 carbon atoms may given methyl, methoxy, ethyl, ethoxy, propyl, propoxy, butyl and butoxy. Preferred such groups and moieties are methyl, methoxy, ethyl and ethoxy, more preferably, methyl and methoxy.

By halogen as used herein is understood chlorine and bromine, more preferably, chlorine.

In the compounds of formula I, M preferably signifies an alkali metal, for example, Na, K, Li, with sodium being more preferred.

The compounds of formula I are fluorescent anionic dyes with a neutral dyeing effect and are generally suitable for dyeing substrates with an affinity for anionic dyes. In particular they are suitable for dying synthetic, semi-synthetic or natural polyamide and/or cellulose fibres, polyurethane fibres or fibres of basically modified polypropylene, or leather. The dyes of formula I are particularly suitable for dyeing synthetic polyamide fibres in a neutral dye bath. Dyeing is effected in manner analogous to the methods known for the dyeing using dyes showing a neutral dyeing effect and suitable for nylon. The tints obtained are even and have good all-round fastness and, in particular, good wash fastness.

The following Examples serve to further illustrate the invention. In the Examples, if not indicated otherwise, the parts and percentages are by weight and the temperatures in degrees Centigrade. The ratio of parts by weight to parts by volume is like the ratio of g to ml.

EXAMPLE 1

10 parts of a compound of formula

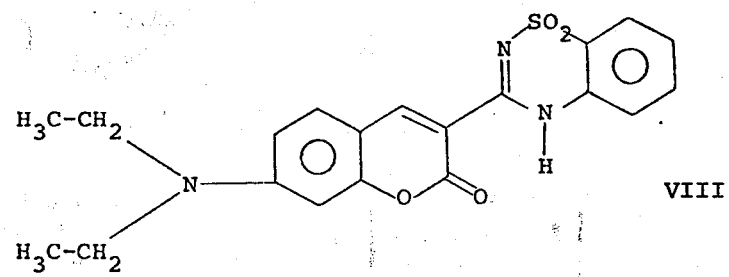

VIII are entered in portions and within 2 to 2½ hours into 130 parts by volume of 25 % oleum at 0°–5° while stirring. Stirring is then continued at 50° for 7 hours, the hot solution poured onto 1000 parts by volume of ice/brine and stirred for another 3 hours. Subsequent filtration yields 12 parts of a red, dry product which is dissolved in hot dimethyl formamide, filtered and treated with ether until turbidity. Filtration and washing and, optionally, recrystallization from water yields the analytically pure product of formula

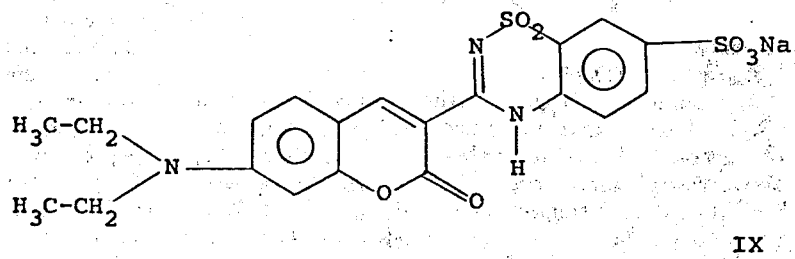

IX

The compound is a yellow dye with green fluorescence which is very water-soluble and most suitable for the dyeing of nylon and wool in a neutral dyebath. The same compound of formula IX is obtained in good yield by replacing the 10 parts of the compound of formula VIII by the corresponding amount of the compound of formula

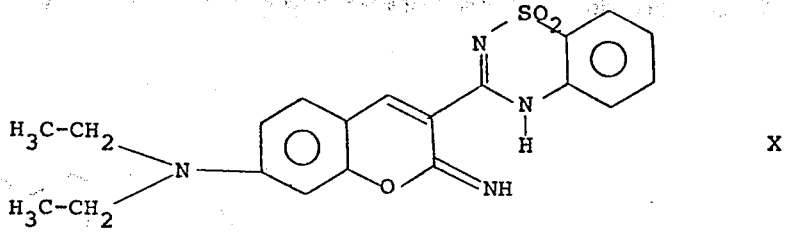

X

Spectroscopic analysis in dimethyl formamide of the compound of formula IX gives the following values $\lambda_{max} = 455$ nm (log $\epsilon = 4{,}75$).

The following Table shows further dyes which may be prepared as described before, for example in the form of sodium salts, and which dye nylon in yellow shades with greenish fluorescences. They correspond to the formula

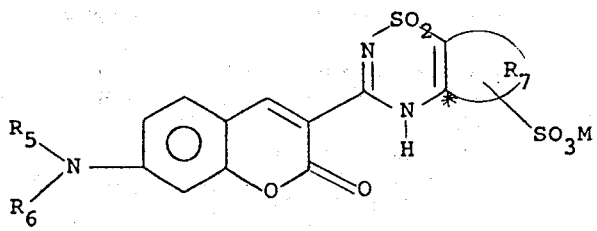

in which $R_5$, $R_6$ and $R_7$ have the significances as shown in the columns

M is sodium, and the ring $R_7$, attached by condensation, is a six-membered ring and the third free linkage corresponds to the connection point with the sulphonic group while the linkage marked by * indicates the connection point with the carbon atom of the formula designated by *

TABLE

| Ex. No. | $-R_5$ | $-R_6$ | $*-R_7-$ |
|---|---|---|---|
| 2 | $-CH_2CH_2CN$ | $-CH_2CH_2CH_3$ | $*-CH=CH-\overset{|}{C}=CH-$ |
| 3 | $-CH_2CH_2CH_2CH_3$ | $-CH_2CH_2CH_2CH_3$ | do. |
| 4 | $-CH_2CH_2CH_3$ | $-CH_2CH_2CH_3$ | do. |
| 5 | $-CH_2CH_2CN$ | $-CH_2CH_2CN$ | do. |
| 6 | $-C_2H_5$ | $-C_2H_5$ | do. |
| 7 | $-CH_2CH_2OC_2H_5$ | $-CH_2CH_2OC_2H_5$ | do. |
| 8 | $-CH_2-CH=CH_2$ | $-C_2H_5$ | do. |
| 9 | $-CH_2CH_2CN$ | H | $*-CH=C(NHCOC_2H_5)-\overset{|}{C}=CH-$ |
| 10 | $-C_2H_5$ | $-C_2H_5$ | $*-CH=C(Cl)-\overset{|}{C}=C(Cl)-$ |
| 11 | do. | do. | $*-\overset{|}{C}=C(Cl)-C(CH_3)=CH-$ |
| 12 | do. | do. | $*-C(CH_3)=CH-\overset{|}{C}=CH-$ |
| 13 | do. | do. | $*-CH=C(CN)-\overset{|}{C}=CH-$ |
| 14 | do. | do. | $*-\overset{|}{C}=CH-C(COOCH_3)=CH-$ |
| 15 | do. | do. | $*-\overset{|}{C}=CH-C(COOC_2H_5)=CH-$ |
| 16 | do. | do. | $*-\overset{|}{C}=CH-C(OCOCH_3)=CH-$ |
| 17 | do. | do. | $*-\overset{|}{C}=CH-C(OCOC_2H_5)=CH-$ |
| 18 | do. | do. | $*-\overset{|}{C}=CH-C(COOCH_2CH_2CH_3)=CH-$ |
| 19 | do. | do. | $*-\overset{|}{C}=CH-C(COOCH_2C_6H_5)=CH-$ |
| 20 | do. | do. | $*-CH=C(NHCOCH_3)-\overset{|}{C}=CH-$ |
| 21 | do. | do. | $*-CH=C(Br)-\overset{|}{C}=CH-$ |
| 22 | do | do | $*-CH=O(OC_2H_5)-\overset{|}{C}=CH-$ |
| 23 | do. | do. | $*-\overset{|}{C}(SO_2NH_2)=CH-C=CH$ |
| 24 | do. | do. | $*-\overset{|}{C}=CH-CH=CH-$ |
| 25 | do. | do. | $*-\overset{|}{C}=CH-C(CN)=CH-$ |
| 26 | do. | do. | $*-\overset{|}{C}=CH-C(CF_3)=CH-$ |
| 27 | do. | do. | $*-C(CH_3)=CH-\overset{|}{C}=C(Br)-$ |
| 28 | do. | do. | $*-C(CN)=CH-\overset{|}{C}=CH-$ |
| 29 | do. | do. | $*-CH=CH-\overset{|}{C}=C(OCH_3)-$ |
| 30 | do. | do. | $*-\overset{|}{C}=CH-CH=C(CN)-$ |
| 31 | do. | do. | $*-N=\overset{|}{C}-N=CH-$ |
| 32 | do. | do. | $*-CH=\overset{|}{C}-N=CH-$ |
| 33 | $-C_2H_5$ | $-C_2H_5$ | $*-CH=C(Cl)-\overset{|}{C}=CH-$ |
| 34 | do. | do. | $*-CH=C(CH_3)-\overset{|}{C}=CH-$ |
| 35 | do. | do. | $*-CH=C(OCH_3)-\overset{|}{C}=CH-$ |

Application Example A

A 50° warm dyebath is prepared containing 1000 parts of water, 2 parts of a sulphonated ester of a high molecular unsaturated fatty acid presenting a sulphonation grade of 99% and 2 parts of ammonium sulphate. Synthetic polyamide fibres, for example nylon 66, are treated for 15 minutes, then 0.16 parts of the dye obtained in accordance with Example 1 are added, the dyebath is warmed to the boiling temperature within 30–45 minutes and boiling is done for one hour.

The dyeing obtained is an even yellow shade with greenish fluorescence presenting good wash fastness. Equally good shades are obtained by replacing, in the above dyeing example, the 0.16 parts of the dye of Example 1 by the corresponding amount of one of the dyes of Examples 2–35.

What is claimed is:

1. A compound, of formula I$a$,

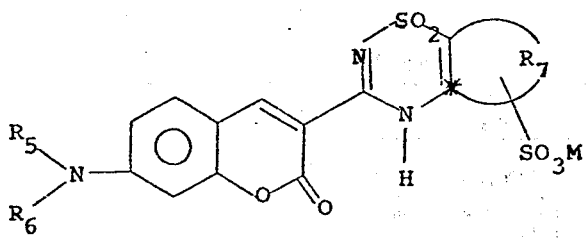

Ia in which each of $R_5$ and $R_6$, which may be the same or different, signifies a hydrogen atom, an alkyl or allyl, radical or an alkyl radical substituted by a halogen atom, an alkoxy or cyano group, which alkyl radicals and alkoxy moieties in such radicals contain 1 to 4 carbon atoms with the proviso that when one of $R_5$ and $R_6$ signifies a hydrogen atom the other has a significance other than hydrogen, $R_7$ signifies a radical of formula $(a)$, $(b)$, $(c)$, $(d)$, or $(e)$

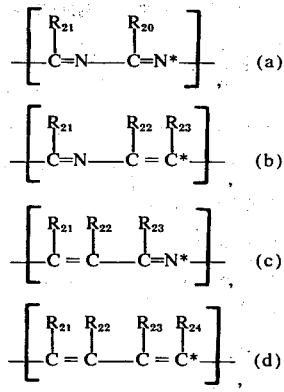

or

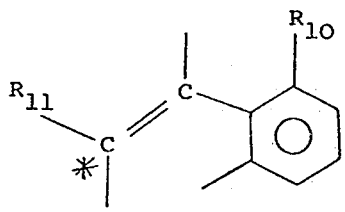

in which $R_{20}$ signifies $SO_3M$, $R_{21}$ signifies a hydrogen chlorine or bromine atom, a alkyl, alkoxy, cyano, thiocyano, trifluoromethyl, alkoxycarbonyl, benzyloxy-carbonyl, alkylcarbonyloxy, alkylcarbonylamino, amino-sulphonyl, alkylamino-sulphonyl or dialkylamino-sulphonyl radical, which alkyl and alkoxy radicals or moieties in such radicals contain 1 to 4 carbon atoms, each of $R_{22}$, $R_{23}$ and $R_{24}$, which may be the same or different, signifies a hydrogen, chlorine or bromine atom, a $SO_3M$, methyl, alkoxy, cyano, thiocyano, trifluoromethyl, alkoxycarbonyl, benzyloxycarbonyl, alkylmethyl, alkylcarbonyloxy, alkylcarbonyl-amino, aminosulphonyl or alkylaminosulphonyl radical, which alkyl and alkoxy radicals or moieties in such radicals contain 1 to 4 carbon atoms, with the proviso that each of radicals of formula $(a)$ $(b)$ $(c)$ and $(d)$ bear only one $-SO_3M$ group and the radical of formula $(d)$ bears not more than two substituents in addition to the $-SO_3M$ group, $R_{10}$ signifies hydrogen, amino-sulphonyl or $-SO_3M$, $R_{11}$ signifies a hydrogen atom or $-SO_3M$ with the proviso that the radical of formula $(e)$ contains only one $-SO_3M$ group, the atom of radical $(a)$ to $(e)$ marked *, being, in each case, bound to the carbon atom designated by the same mark in formula I$a$, and M is hydrogen or an alkali metal.

2. A compound according to claim 1, of formula I$b$,

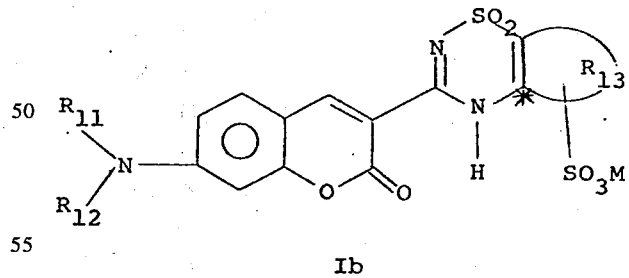

Ib in which each of $R_{11}$ and $R_{12}$, which may be the same or different, signifies a methyl or ethyl or allyl radical, or a methyl or ethyl radical substituted by a cyano or alkoxy group of 1 to 4 carbon atoms, $R_{13}$ signifies a radical of formula $(b')$, or $(d')$,

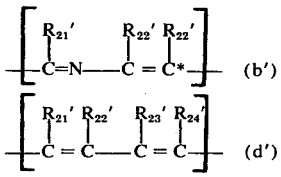

in which
R₂₁' signifies a hydrogen, chlorine or bromine atom, a methyl, methoxy, ethoxy, cyano, trifluoromethyl, alkoxycarbonyl, alkyl-carbonyloxy, alkylcarbonyl amino or aminosulphonyl radical which alkyl and alkoxy moieties contain 1 to 4 carbon atoms, each of R₂₂', R₂₃' and R₂₄', which may be the same or different, signifies a hydrogen, chlorine or bromine atom, a SO₃M, methyl, methoxy, ethoxy, cyano, trifluoro-methyl alkoxycarbonyl, alkylcarbonyloxy, alkyl-carbonylamino or amino-sulphonyl radical, which alkyl and alkoxy moieties contain 1 to 4 carbon atoms, with the proviso that the radicals (b') and (d') bear only one —SO₃M group and the radical (d') bears not more than two substituents in addition to the —SO₃M group, the mark * has the same significance as defined in claim 1 and M is as defined in claim 1.

3. A compound according to claim 1, in which, in the radical of formula (b), R₂₂ is —SO₃M.

4. A compound according to claim 1, in which, in the radical of formula (c), R₂₂ is —SO₃M.

5. A compound according to claim 1, in which, in the radical of formula (d), R₂₂ is —SO₃M.

6. A compound according to claim 1, in which, in the radical of formula (d), where R₂₂ signifies other than a hydrogen atom or a —SO₃M group, R₂₃ signifies SO₃M.

7. A compound according to claim 2, in which, in the radical of formula (b'), R₂₂' signifies —SO₃M.

8. A compound according to claim 2, in which, in the radical of formula (d'), R₂₂' signifies —SO₃M.

9. A compound according to claim 2, in which, in the radical of formula (d'), where R₂₂' signifies other than a hydrogen atom or a SO₃M group, R₂₃' signifies —SO₃M.

10. A compound according to claim 2, of formula Ic,

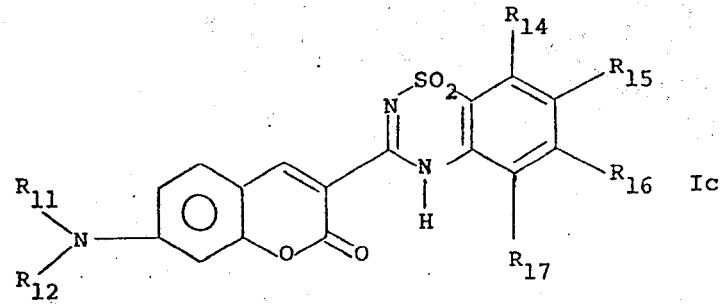

in which
R₁₁ and R₁₂ are as defined in claim 2, each of
R₁₄ signifies a hydrogen, chlorine or bromine atom, a methyl, methoxy, ethoxy or trifluoromethyl radical, each of
R₁₅, R₁₆ and R₁₇ signifies —SO₃M or a hydrogen, chlorine or bromine atom, a methyl, methoxy, ethoxy or trifluoromethyl radical, with the proviso that one of R₁₅, R₁₆ and R₁₇ signifies SO₃M and at least one of R₁₄, R₁₅, R₁₆ and R₁₇ signifies a hydrogen atom.

11. A compound according to claim 10, in which at least two of R₁₄, R₁₅, R₁₆ and R₁₇ signify a hydrogen atom.

12. A compound according to claim 11, in which R₁₅ signifies a —SO₃M group, each of R₁₄ and R₁₇ signifies a hydrogen atom and R₁₆ signifies a hydrogen, chlorine, bromine, methoxy, ethoxy or trifluoromethyl radical.

13. A compound according to claim 12, in which R₁₆ signifies a hydrogen atom.

14. A compound according to claim 1, of formula

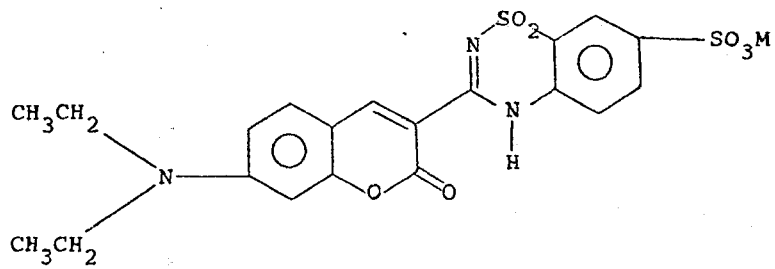

in which M is as defined in claim 1.

15. A compound according to claim 1, of formula

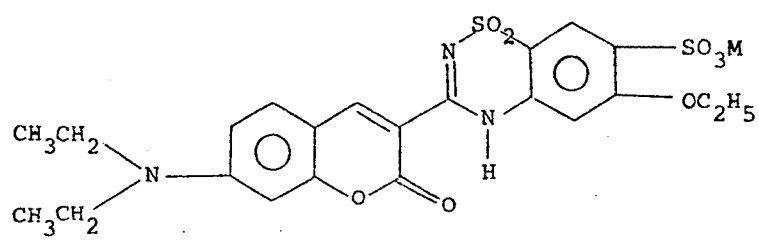

in which M is as defined in claim 1.
16. A compound according to claim 1, of formula
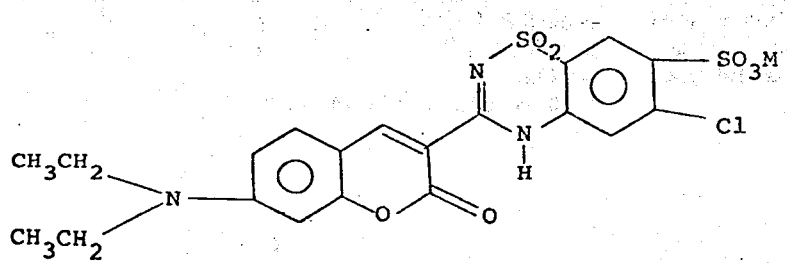
in which M is as defined in claim 1.
17. A compound according to claim 1, of formula
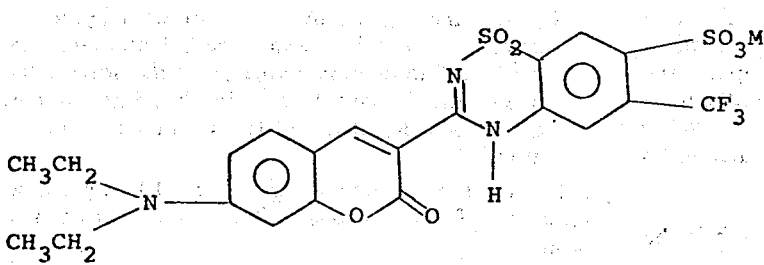
in which M is as defined in claim 4.
18. A compound according to claim 1, of formula
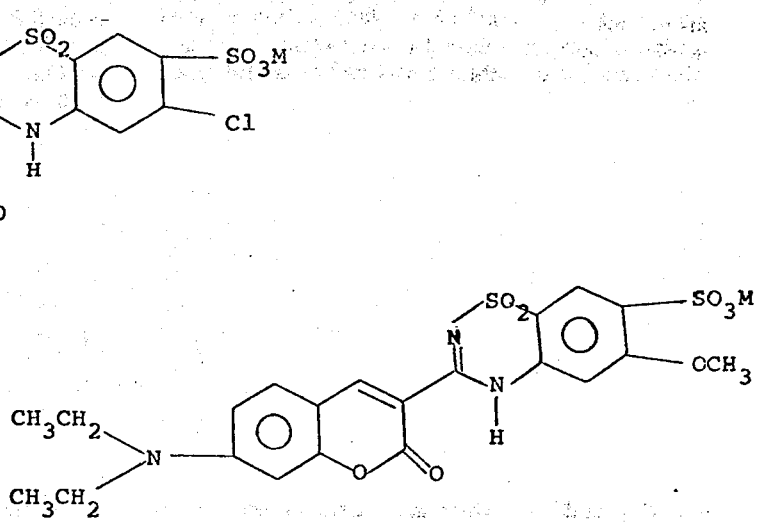
in which M is as defined in claim 1.
19. A compound according to claim 1, in which M is sodium.
* * * * *